United States Patent [19]

Bible

[11] Patent Number: 5,226,424
[45] Date of Patent: Jul. 13, 1993

[54] LOW ENERGY CONSUMPTIVE DEVICE FOR ACQUISITION OF DATA RELATING TO ABNORMAL HEART MUSCLE ACTIVITY

[75] Inventor: Christopher T. Bible, Reno, Nev.

[73] Assignee: Caliber Medical Corporation, Reno, Nev.

[21] Appl. No.: 701,799

[22] Filed: May 17, 1991

[51] Int. Cl.$^5$ .............................................. A61B 5/04
[52] U.S. Cl. .................................................. 128/696
[58] Field of Search ............... 128/696, 703, 704, 705, 128/708, 695

[56] References Cited

U.S. PATENT DOCUMENTS

| | | | |
|---|---|---|---|
| 3,794,841 | 2/1974 | Consentino et al. | 250/199 |
| 3,903,874 | 9/1975 | Shakespeare | 128/696 |
| 4,216,462 | 8/1980 | McGrath et al. | 340/150 |
| 4,417,306 | 11/1983 | Citron et al. | 128/703 |
| 4,531,527 | 7/1985 | Reinhold, Jr. et al. | 128/696 |
| 4,580,295 | 4/1986 | Richman | 359/110 |
| 4,974,599 | 12/1990 | Suzuki | 128/696 |

OTHER PUBLICATIONS

Thaler, Malcomm S., *The Only EKG Book For You'll Ever Need*, J. B. Lippincott & Co., 1988. pp. 8-29.
Pepine, Carl J., "Technical Requirements of Ambulatory ECG Monitoring", *The Journal of Myocardial Ischemia*, Jun. 19, 1989, pp. 8-29.

Primary Examiner—Lee S. Cohen
Assistant Examiner—Samuel Gilbert
Attorney, Agent, or Firm—Nydegger & Associates

[57] ABSTRACT

A portable low energy consumptive device and method for monitoring heart muscle electrical activity includes a plurality of electrical contacts and a signal processing unit. The contacts receive an electrical signal generated by the heart muscle of a patient and deliver the signal in analog form to the signal processing unit which contains an analog signal processor, an A/D converter, a digital microprocessor, and a memory. The unit triplicates the signal and processes each of the three signals separately in the analog signal processor. The processed signals are then converted to three distinct digital data sets, the first of which is stored in memory while the remaining two are processed in the microprocessor to determine ST segment characteristics useful in diagnosing myocardial ischemia. Although the device operates continuously, only a portion of the operating time is devoted to digital data processing which has a higher energy demand. The remainder of the operating time is devoted to analog signal processing or data storage which have a lower energy demand.

19 Claims, 3 Drawing Sheets

LOW ENERGY CONSUMPTIVE DEVICE FOR ACQUISITION OF DATA RELATING TO ABNORMAL HEART MUSCLE ACTIVITY

FIELD OF THE INVENTION

The present invention relates generally to monitoring heart muscle electrical activity. More particularly, the present invention relates to an apparatus and method for detecting abnormal heart muscle electrical activity. The present invention particularly, though not exclusively, relates to an apparatus and method for detecting myocardial ischemia by measuring deviations in the ST segment.

BACKGROUND OF THE INVENTION

A restricted blood supply to the heart muscle is a condition termed myocardial ischemia which is evidenced by abnormal heart muscle electrical activity. Untreated, myocardial ischemia can ultimately result in heart failure. As a result, monitoring of the electrical signals corresponding to heart muscle activity is an invaluable diagnostic tool for determining the health of the heart and identifying abnormalities thereof.

When the electrical signal of a heart muscle is plotted over time, it defines a characteristic curve having a waveform which extends periodically above and below a horizontal reference axis conventionally termed the isoelectric line. Each elevation or depression of the signal curve above or below the reference axis respectively is termed a wave and is identified by a letter. There are a total of six waves in each period of the signal which are identified by the letters, P, Q, R, S, T, and U. A straight line connecting two waves of the signal curve is further identified as a segment, while a wave and connecting straight line is termed an interval. Segments and intervals are identified by various combinations of the above-listed letters.

A normal electrical signal of a healthy heart muscle is generally reflected in a regular curve having predictable PR and ST segments and PR, QRS, and QT intervals. Anomalous electrical signals of a heart muscle are reflected by deviations in specific portions of the curve from the predicted norm. Such deviations may be symptomatic of myocardial ischemia.

More particularly, the ST segment deviations are known to be a key indicator of myocardial ischemia. The ST segment of a typical healthy heart is a straight line of zero slope on or near a horizontal reference axis. If the ST segment is parallel to the reference axis, but is elevated or depressed by a significant deviation from the reference axis, the heart muscle signal is termed anomalous which may be indicative of an unhealthy heart muscle. Likewise, an ST segment exhibiting a significant positive or negative slope, may further be indicative of an unhealthy heart.

Conventional electrical monitoring devices exist which are capable of characterizing the ST segment. However, such devices are usually relatively immobile and complex to operate which requires them to be maintained in a central medical facility for operation by skilled personnel. As a result, outpatients at such facilities only receive monitoring periodically and for relatively short time durations. Diagnosis of myocardial ischemia generally requires the compilation of signal histories for an extended period of time which periodic monitoring does not provide.

Portable monitors for heart muscle electrical activity represent a potential solution to this problem. Unfortunately, however, satisfactory portable monitors have not been developed which are compact, yet which have the capabilities of a clinical monitor. Known portable devices are often not sufficiently accurate or sensitive to detect small deviations in the heart muscle electrical signal, and particularly in the ST segment. Such deviations can be critical to the diagnosis of myocardial ischemia.

One reason for the lack of accuracy and sensitivity in portable monitors is that high-quality diagnostic data acquisition requires a relatively large power source. However, portable monitors by necessity rely on relatively small disposable or rechargeable power packs. The frequency with which the user would have to replace or recharge the power packs to produce diagnostic data equivalent to that produced by clinical monitors would be so great with known technology as to render such monitors impracticable.

As such, a solution to these problems is needed. Specifically, a low energy consumptive portable heart monitor is needed for acquiring diagnostic data. A portable heart monitor is particularly needed for acquiring data relating to the ST depression which is sufficiently sensitive to enable adequate detection and quantification of myocardial ischemia.

SUMMARY OF THE INVENTION

The present invention is a monitoring device and method of using the same for acquiring data relating to abnormal electrical activity in the heart muscle of a patient. The device comprises a plurality of electrical contacts and a portable self-contained signal processing unit in communication therewith. The device is designed to operate in conjunction with structurally separate data transmission and data display units. The contacts are positionable on a patient to receive electrical signals which are generated by the electrical activity of the patient's heart muscle. Electrical signals so received are transmitted via a direct line to the signal processing unit which is affixed to the patient for conversion to meaningful diagnostic data.

Throughout a given heart monitoring period the signal processing unit repetitively performs a specific sequence of functions. In particular, the signal processing unit establishes a reference axis for each signal, identifies the ST segment of each signal, and compares the ST segment with the reference axis to measure the extent to which the ST segment deviates above or below the reference axis. This quantity, which is termed the measured ST deviation, is compared to a predetermined threshold deviation of the ST segment which is stored in the memory of the signal processing unit.

When the signal processing unit first detects an ST deviation which exceeds the predetermined threshold ST deviation, the signal processing unit identifies this measured ST segment as an anomalous ST segment deviation initiating an event of interest. The associated signal is then stored in the internal memory of the signal processing unit while it continues to search for further anomalous ST deviations. Consecutive signals having anomalous ST deviations constitute an episode. For each episode, the signal processing unit stores the first signal of the episode as noted above, the last signal of the episode, and the signal representing the maximum ST deviation of the episode, if there is such a maximum. To supplement these stored signals, associated data such as slope of the anomalous ST segments, duration of the episode and heart rate are also stored. This data storage procedure is repeated for each occurrence of a new episode.

The signals and associated data stored by the present device can be displayed by transmitting them from the signal processing unit to a remote display unit via a data transmission unit. Upon receiving the recorded signals and associated data from the signal processing unit for each episode, the display unit has the ability to print out the signals in graphical form along with the associated data in a summary report therewith.

The signal processing unit operates continuously throughout the heart monitoring period in one of two modes of energy demand. The first operating mode is a conservation mode of relatively lower energy demand which constitutes the majority of the monitoring period. The second operating mode is a normal mode of relatively higher energy demand which constitutes the remainder of the monitoring period. The two modes of operation are enabled by aligning a series of components within the signal processing unit including a signal reproducer, an analog signal processor, an analog to digital (A/D) converter, a digital microprocessor, a memory, and a data output. The signal processing unit is further provided with a clock in communication with the microprocessor and a power pack which supplies the energy requirements of each of the above-listed components.

Operation of the signal processing unit is initiated when a pair of electrical contacts on the patient communicates an electrical signal of the heart muscle to the signal reproducer in the form of a conventional analog electrocardiogram (ECG) signal. The signal reproducer triplicates the received signal into three identical analog copies of the original signal. Each analog signal is then uniquely processed in the analog signal processor to produce three different analog signals which are subsequently converted in the A/D converter into three distinct digital data sets. The first data set is the digital form of the original ECG signal, the second data set is an enhancement of the PR and ST segments and the third data set is an enhancement of the QRS interval. The digital microprocessor which is the primary energy consumer of the unit, is at rest throughout these analog steps, and consequently the unit operates in the mode of lower energy consumption during this time.

At periodic predetermined intervals which correspond approximately to the creation of the three data sets, the clock initiates the digital data processing function of the microprocessor, thereby switching the unit into the mode of higher energy consumption. The digital data processing function only relates to the second and third data sets because the first data set has already been stored in the temporary memory of the unit. The microprocessor performs digital data processing by initially evaluating the third data set to determine the validity of the signal from which the data set is derived. If the signal is validated, the microprocessor uses the second data set to establish the reference axis and determine the ST deviation. If the ST deviation exceeds the predetermined threshold, the anomalous ST deviation and associated signal of the first data set are transferred to permanent memory.

When the digital data processing function is completed, the microprocessor goes back to its resting state. Correspondingly, the signal processing unit returns to the conservation mode of low energy consumption and awaits the next electrical signal from the contacts for analog signal processing. The microprocessor does not resume digital data processing until it is reset by the clock after the next predetermined time interval expires. The actual time that the microprocessor is processing digital data is relatively short in comparison to the time it is at rest. Accordingly, the overall energy consumption of the unit throughout the monitoring period is considerably lower than if the microprocessor were processing digital data continuously.

It is apparent that the present invention provides a device and method operable in a low mode of energy consumption throughout much of its operating life without substantially diminishing the effectiveness of the device for diagnosing heart muscle electrical anomalies, and in particular for diagnosing myocardial ischemia. The ability of the device to operate with overall lower energy consumption derives from the fact that processing of the analog data, as performed in the conservation operating mode, requires considerably less energy than does processing the digital data in the normal operating mode, whereas conventional heart monitoring devices process digital data continuously. It has been found that the present device and method are particularly advantageous in relation to portable heart monitors, enabling them to acquire diagnostic data of a quality approaching that of clinical monitors coupled with their inherent mobility.

The novel features of this invention, as well as the invention itself, both as to its structure and its operation, will be best understood from the accompanying drawings, taken in conjunction with the accompanying description, in which similar reference characters refer to similar parts, and in which:

BRIEF DESCRIPTION OF THE DRAWINGS

FIG. 4 is a generalized plot of a normal heart muscle electrical signal versus time.

DESCRIPTION OF PREFERRED EMBODIMENTS

Figure 1:
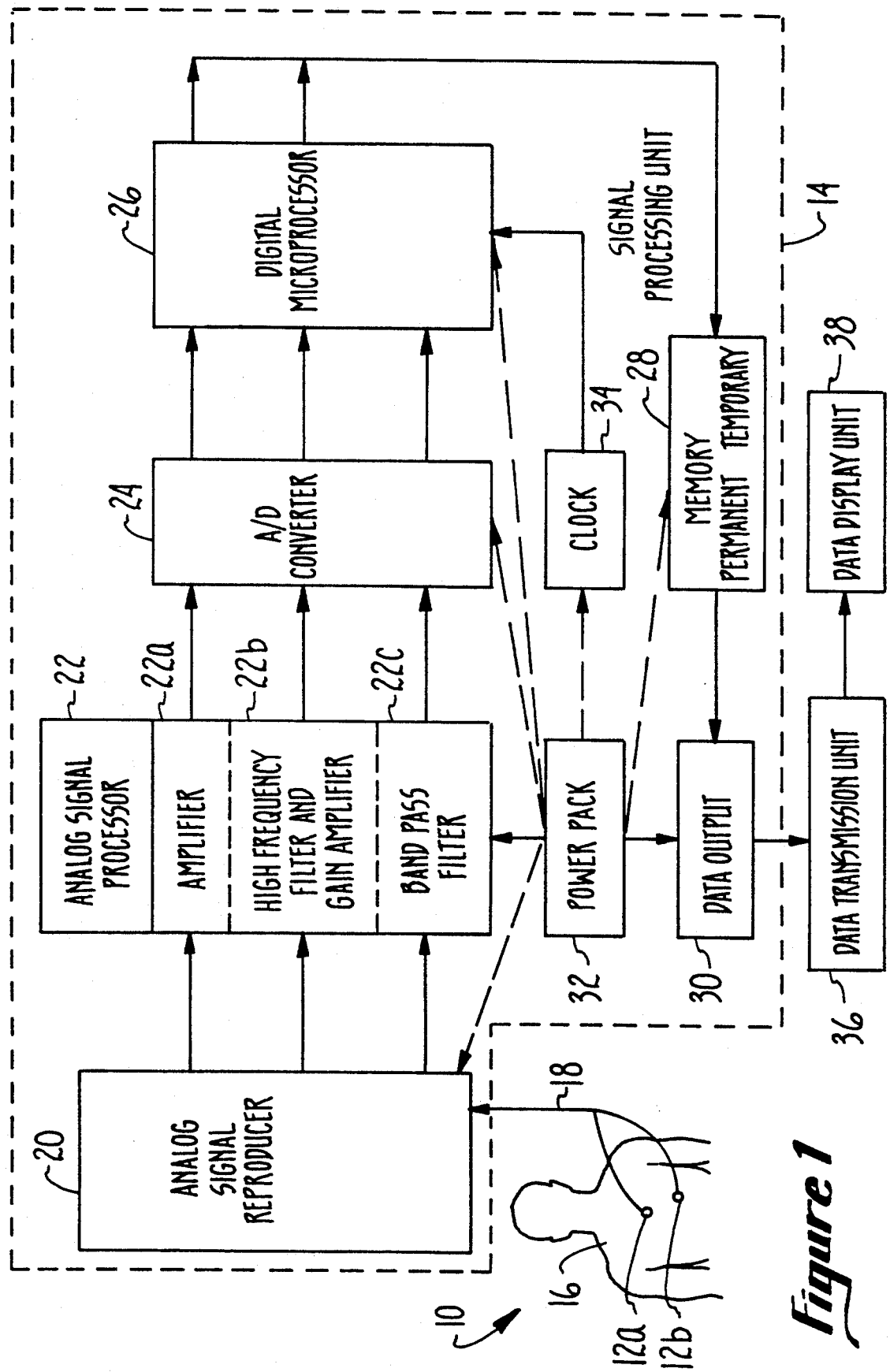
FIG. 1 is a schematic of the monitoring device of the present invention.

Referring initially to the schematic of FIG. 1, the heart monitoring device of the present invention is generally designated 10 and comprises a pair of heart monitor electrical contacts 12a, 12b and a signal processing unit 14 having a plurality of components integrated within the dashed box representative of unit 14. Contacts 12a, 12b are positioned on the body of patient 16 and are in electrical communication with signal processing unit 14 across a signal conductive line 18. Signal processing unit 14 is preferably self-contained within a portable casing which is affixable to the patient 16 or to the patient's clothing for continuous monitoring of patient 16 throughout the patient's everyday activities.

The internal components of signal processing unit 14 are functionally positioned in series within the unit 14 beginning with an analog signal reproducer 20 capable of producing copies of an analog signal. An analog signal processor 22 follows which may be broken down into three discrete signal pathways 22a, 22b, 22c. First signal pathway 22a comprises an amplifier which amplifies analog signals within a preferred frequency range of 0.05 to 40 Hz. Second signal pathway 22b comprises a high frequency filter and a gain amplifier which in series remove the high frequency range from the analog signal and amplify the resulting filtered analog signal within a preferred frequency range of 0.05 to 25 Hz. Third signal pathway 22c comprises a band pass filter which selectively allows passage of a portion of the analog signal. The preferred portion of the analog signal is a narrow range at or near about 16 Hz.

Signal pathways 22a, 22b, 22c proceed to an analog to digital converter 24 which in turn is followed by a digital microprocessor 26, a memory 28, and finally a data output 30. Memory 28 is divided into temporary memory 28a and permanent memory 28b. Temporary memory 28a is a continuous memory loop which is "temporary" in the sense that data entered therein is continuously displaced out of memory loop 28a by subsequently entered data. Permanent memory 28b is "permanent" in the sense that data entered therein remains in permanent memory 28b indefinitely until the operator takes active steps to remove the data by means such as data transfer or data deletion.

A power pack 32 and a clock 34 are further provided within signal processing unit 14. Power pack 32 is shown connected to each component of unit 14 by a dashed line which indicates that power pack 32 directs internally stored energy to each component and accordingly provides the operating energy requirements for the entire unit 14 power pack 32 is preferably a conventional 9 volt disposable battery which has a producing life of at least about 96 hours when unit 14 is operated in the manner described below. Memory 28 may also be provided with its own independent power backup (not shown) in the event power pack 32 fails, thereby avoiding the loss of stored data. The backup is preferably a lithium battery having a lifetime of several years.

Clock 34 is a pulse timer which communicates directly with microprocessor 26. Clock 34 generates a fixed number of pulses within a predetermined time period which are counted by microprocessor 26 to determine relative time. A preferred pulse rate for clock 34 is 128 pulses per second or about 1 every 7.8 milliseconds (ms).

FIG. 1 shows a data transmission unit 36 and a data display unit 38 with which heart monitoring device 10 of the present invention may interact for expanded data storage as well as data display and distribution. As described in my copending patent application Ser. No. 07/701,780, entitled "Device For Detecting Abnormal Heart Muscle Activity", filed May 17, 1991, incorporated herein by reference, data transmission unit 36 preferably contains a memory for receiving data from output 30 of signal processing unit 14 and a modem for sending the stored data to remote display unit 38 which is preferably a central processing unit having expanded data storage capacity as well as data printout and printout transmission capabilities.

METHOD OF OPERATION

The data acquisition method of the present invention is now described in terms of device 10 and with reference to FIGS. 1-5. Contact pair 12 is positioned on patient 16 in a manner known to one skilled in the art to receive heart muscle electrical signals. Contacts 12a, 12b are preferably positioned on the chest of patient 16 at opposite sides of the heart. When the heart muscle generates electrical signals, which correlate to heart muscle activity, contacts 12a, 12b receive the signals and transmit them to signal processing unit 14 across line 18 in an analog format.

Signal processing unit 14 operates continuously in one of two modes of energy demand, a first energy conservation mode wherein energy demand is lower and a second normal energy consumption mode wherein energy demand is higher, albeit within normally acceptable limits. While the analog signal is being received across line 18 and subsequently processed, unit 14 operates in the conservation mode. In the initial analog step, the heart muscle electrical signal conveyed by line 18 enters analog signal reproducer 20 which reproduces three identical copies of the signal all having the form of a conventional analog ECG signal. The three identical analog signals are then conveyed to analog signal processor 22 which has three discrete signal pathways 22a, 22b, 22c.

Figure 2A:
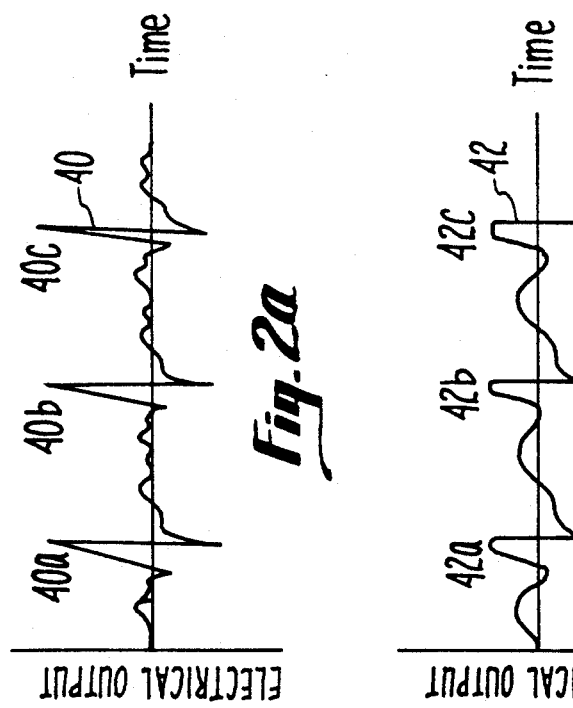
FIG. 2a is an analog plot of an amplified heart muscle electrical signal versus time.

The first analog signal is sent through signal pathway 22a which is made up of an amplifier which amplifies analog signals within a preferred frequency range of 0.05 to 40 Hz. FIG. 2a shows three representative periods 40a, 40b, 40c of the amplified signal 40 resulting from pathway 22a. Signal 40 is a diagnostic-quality conventional analog ECG signal which is sent to A/D converter 24 and converted to a first digital data set which is nothing more than a digital translation of signal 40. This first digital data set is sent to memory loop 28a via microprocessor 26 for temporary storage while the signals resulting from pathways 22b and 22c are processed.

Figure 2B:
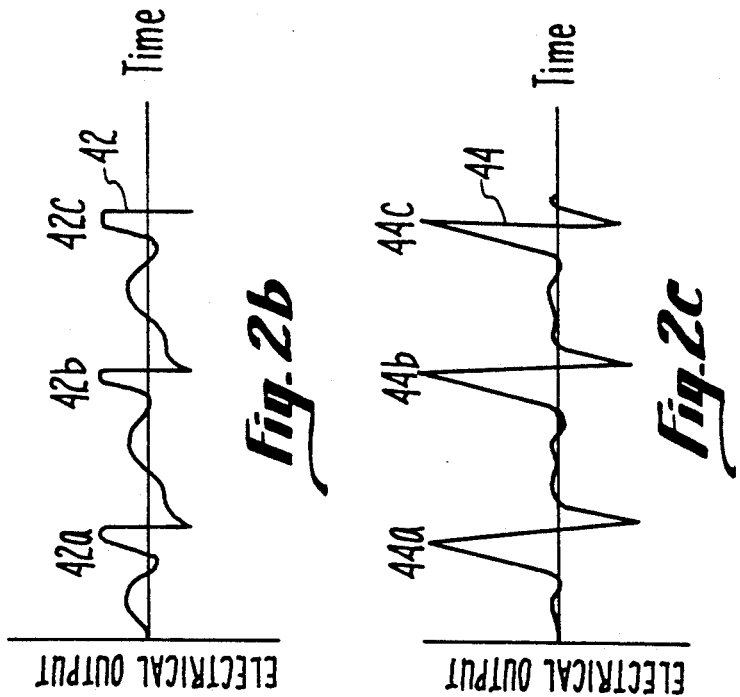
FIG. 2b is an analog plot of a high frequency filtered and amplified heart muscle electrical signal versus time.

Second signal pathway 22b is a high frequency filter and a gain amplifier which in series remove the high frequency range from the analog signal and amplify the resulting filtered analog signal within a preferred frequency range of 0.05 to 25 Hz. FIG. 2b shows three representative periods 42a, 42b, 42c of the filtered and amplified signal 42 resulting from pathway 22b. Signal 42 is generated for conversion to a second data set in A/D converter 24. Second data set is used to facilitate identification and enhancement of the PR and ST segments of the signal curve when processed within microprocessor 26 in a manner to be described hereafter.

Figure 2C:
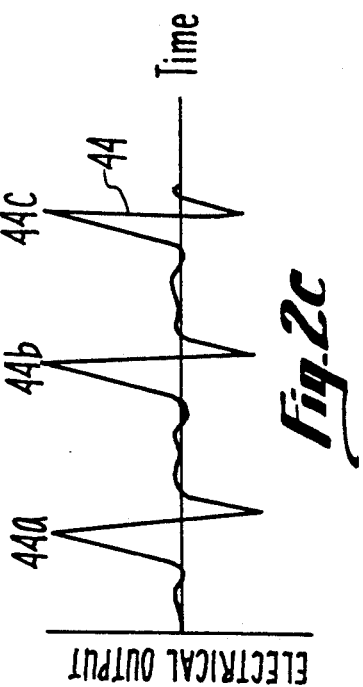
FIG. 2c is an analog plot of a band pass filtered heart muscle electrical signal versus time.

Third signal pathway 22c is a band pass filter which selectively allows the passage of the portion of the analog signal in a preferred vicinity of 16 Hz. FIG. 2c shows three representative periods 44a, 44b, 44c of the band pass filtered signal 44 resulting from pathway 22c. Signal 44 is generated for conversion to a third data set in A/D converter 24. Third data set facilitates identification and enhancement of the QRS interval and validation of the signal when processed within microprocessor 26 in conjunction with second data set.

As noted above, unit 14 is in an energy conservation mode during operation of analog signal reproducer 20, analog signal processor 22 and A/D converter 24 because digital microprocessor 26, which is the primary energy consumer of unit 14, is at rest throughout these analog operations. However, clock 34 signals microprocessor 26 to activate for digital data processing about once every 7.8 ms which corresponds approximately to the creation of the three digital data sets. Upon activation of microprocessor 26, signal processing unit 14 goes into the normal mode of higher energy consumption.

Figure 3:
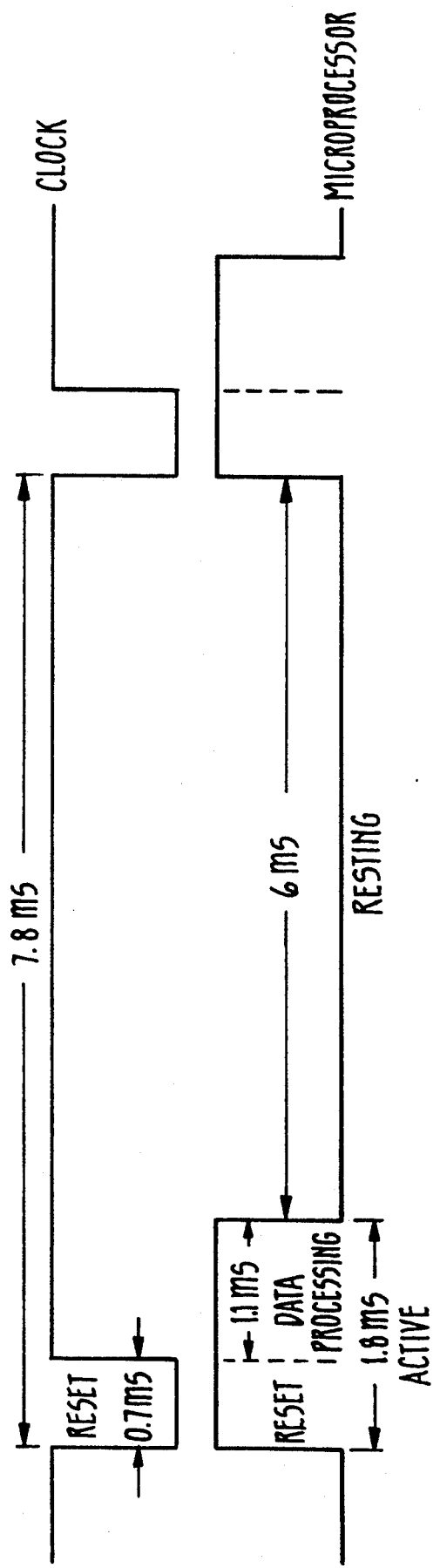
FIG. 3 is a plot of time lines for microprocessor and clock operation.
Figure 1:
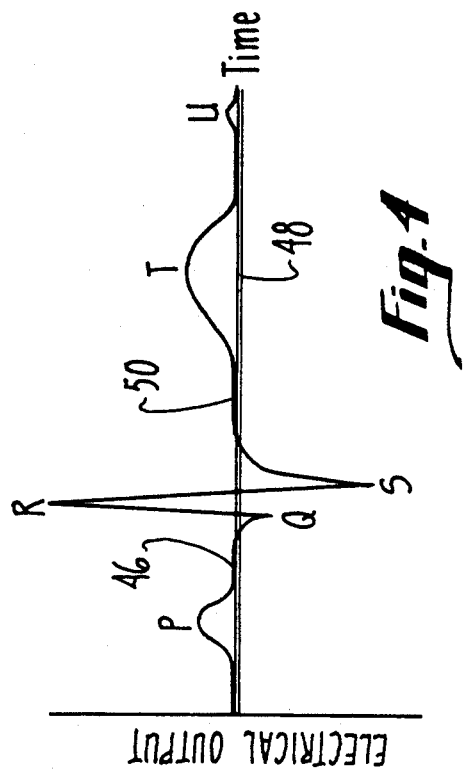

The time sequence of the energy modes is described with reference to the time lines of FIG. 3. At the start of each 7.8 ms interval, clock 34 interacts with microprocessor 26 to initiate a reset function which activates the data processing function of microprocessor 26. Resetting requires about 0.7 ms wherein microprocessor 26 stabilizes sufficiently to perform digital data processing. Thereafter, microprocessor 26 performs digital data processing of second and third data sets within a required time duration of about 1.1 ms. When data processing is completed, microprocessor 26 returns to a resting state wherein it performs no data processing until clock 34 initiates the next reset function. Thus, microprocessor 26 is in a resting state for about 6 ms of each 7.8 ms interval.

The reset and digital data processing functions of microprocessor 26 correspond to the high energy mode of operation, while the resting state of microprocessor 26 corresponds to the low energy mode of operation. Therefore, signal processing unit 14 operates in the high energy mode for less than 25% of the continuous heart monitoring period. Low energy consumptive operation of unit 14 extends the life of power pack 34 without sacrificing data processing capabilities. Thus, unit 14 is able to perform its monitoring function for several days independent of any external support and without requiring power pack renewal.

Referring now to FIGS. 2b and 2c, digital data processing in microprocessor 26 comprises initially evaluating the QRS interval from the third data set to determine the validity of signal 44 from which the third data set is derived. If signal 44 is validated, microprocessor 26 evaluates the second data set which is a digital representation of signal 42.

Figure 5:
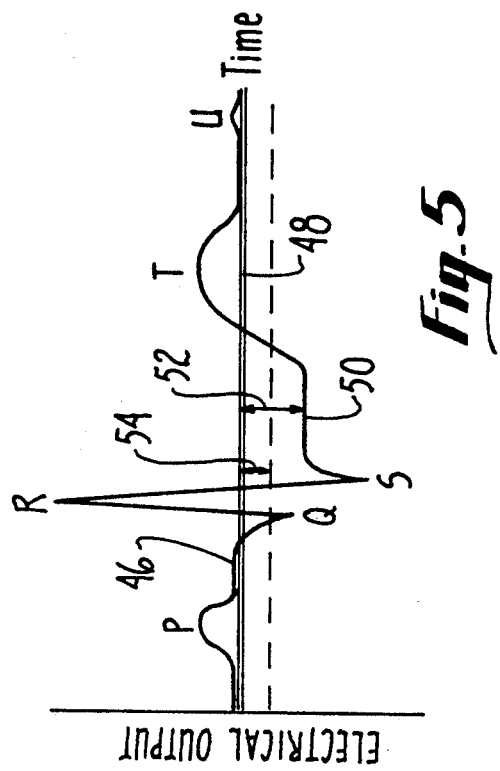
FIG. 5 is a generalized plot of an anomalous heart muscle electrical signal versus time.

Referring next to FIGS. 4 and 5, which graphically show a generalized period of a normal heart muscle electrical signal and a single period of an anomalous signal respectively, microprocessor 26 uses PR segment 46 of the second data set to establish reference axis 48 for each given signal. Microprocessor 26 then identifies ST segment 50 of each signal and compares ST segment 50 with reference axis 48 to measure the extent to which ST segment 50 deviates above or below reference axis 48. This quantity, denoted as 52 in FIG. 5, is termed the measured ST deviation. Microprocessor 26 compares ST deviation 52 to predetermined threshold ST segment deviation 54 which is stored in permanent memory 28b of signal processing unit 14.

When microprocessor 26 first detects an ST deviation 52 which exceeds predetermined threshold ST deviation 54, such as shown in FIG. 5, microprocessor 26 identifies this measured ST segment deviation 52 as an anomalous ST segment deviation initiating an event of interest. The associated signal is then temporarily stored in memory 28a as noted above while microprocessor 26 continues to evaluate incoming signals in search of further anomalous ST deviations. Consecutive signals having anomalous ST deviations constitute an episode.

If microprocessor 26 observes an episode, it transfers the temporarily stored signal 40, which represents the first signal of the episode, to permanent memory 28b. For each episode, signal processing unit 14 also stores in permanent memory 28b the value of every ST deviation as well as the last signal of the episode and the signal representing the maximum ST deviation of the episode, if there is such a maximum. To supplement the stored anomalous deviation values and selected corresponding signals, other associated data including slope of the anomalous ST segments, duration of the episode and heart rate are also determined by microprocessor 26 and stored in permanent memory 28b. This data storage procedure is repeated for each occurrence of a new episode.

The signals and associated data stored in memory 28b can be displayed by first outputting the data from memory 28b to data output 30 which is interfaced with data transmission unit 36 by means such as an optical coupling. Data transmission unit 36 has a memory to receive the data in anticipation of transmission to remote display unit 38 by means such as a modem contained within data transmission unit 36 and a connected telephone line. Display unit 38 prints out the data received thereby in graphical form with respect to the recorded signals, ST deviation trend, and heart rate. The remaining associated data is printed out numerically in the form of a summary report.

Although the present invention has been described with reference to individual processing of single signals to establish the occurrence of ischemic events, it is understood that within the scope of the present invention averages of multiple consecutive signals can be determined from individual signals and such averages can be used in place of individual signals to establish the occurrence of ischemic events. Furthermore, the present invention has been described with reference to a single data channel fed to signal processing unit 14 from one pair of contacts 12 on patient 16. However, it is understood that signal processing unit 14 may be provided with the capability of processing a plurality of data channels in parallel within the scope of the present invention by providing duplicate contact pairs on other locations of patient 16 and duplicative components within unit 14.

While certain preferred conditions, quantities and other parameters were detailed in the above description of preferred embodiments, those can be varied, where suitable, with similar results. Various applications, variations and ramifications of this invention will occur to those skilled in the art upon reading the present disclosure. Those are intended to be included within the scope of this invention as defined in the appended claims.

I claim:

1. An energy conserving device for monitoring heart muscle electrical activity of a patient comprising:
    a plurality of electrical contacts adapted to be affixed to the patient; and
    a signal processing unit in communication with said contacts and having in series an analog signal reproducer, an analog signal processor, an analog to digital converter, a digital microprocessor and a memory.

2. An energy conserving device for monitoring heart muscle electrical activity of a patient as recited in claim 1 wherein said analog signal processor has first, second and third signal pathways, said first signal pathway comprising an amplifier, said second signal pathway comprising a high frequency filter, and said third signal pathway comprising a band pass filter.

3. An energy conserving device for monitoring heart, muscle electrical activity of a patient as recited in claim 1 wherein said signal processing unit has a clock in communication with said microprocessor to activate digital data processing functions of said microprocessor.

4. An energy conserving device for monitoring heart muscle electrical activity of a patient as recited in claim 1 wherein said signal processing unit has a power pack to provide operating energy to said signal processing unit.

5. An energy conserving device for monitoring heart muscle electrical activity of a patient as recited in claim 1 wherein said signal processing unit is self-contained and portable.

6. An energy conserving device for monitoring heart muscle electrical activity of a patient comprising:
   a plurality of electrical contacts adapted to be affixed to the patient; and
   a signal processing unit in communication with said contacts and having in series an analog signal reproducer, an analog signal processor, an analog to digital converter, a digital microprocessor, a memory and a data output, said data output comprising an optical transmitter capable of communication with an optical receiver of a data transmission unit external to said signal processing unit.

7. An energy conserving device for monitoring heart muscle electrical activity of a patient comprising:
   contact means affixable to the patient for receiving an electrical heart muscle signal in an analog format generated by the patient;
   reproducing means for triplicating said analog heart muscle electrical signal into first, second and third identical analog signals;
   a first filtering means for high frequency filtering said second analog signal to enhance PR and ST segments of said second analog signal;
   a second filtering means for band pass filtering said third analog signal to enhance QRS interval of said third analog signal;
   a conversion means for converting said first, second, and third analog signals to first, second and third digital data sets respectively;
   a digital data processing means for processing said second and third data sets to determine an ST segment deviation associated with said first analog signal; and
   a memory means for storing said first data set.

8. An energy conserving device for monitoring heart muscle electrical activity of a patient as recited in claim 7 further comprising a timing means for activating said digital data processing means after creation of said first, second, and third data sets.

9. An energy conserving device for monitoring heart muscle electrical activity of a patient as recited in claim 7 further comprising an amplifying means for amplifying said first analog signal.

10. An energy conserving method for monitoring heart muscle electrical activity of a patient employing a portable signal processing unit affixable to the patient, the method comprising:
   a) obtaining from the patient an electrical heart muscle signal in an analog format and delivering said electrical heart muscle signal to said signal processing unit;
   b) triplicating said analog heart muscle electrical signal into first, second and third identical analog signals;
   c) high frequency filtering said second analog signal to enhance PR and ST segments of said second analog signal;
   d) band pass filtering said third analog signal to enhance QRS intervals of said third analog signal;
   e) converting said first, second, and third analog signals to first, second and third digital data sets respectively;
   f) processing said second and third digital data sets to determine an ST segment deviation associated with said first analog signal; and
   g) storing said first data set in a temporary memory.

11. An energy conserving method for monitoring heart muscle electrical activity of a patient as recited in claim 10 further comprising initiating step f) in response to a periodic signal from a timing means.

12. An energy conserving method for monitoring heart muscle electrical activity of a patient as recited in claim 10 further comprising amplifying said first analog signal prior to step e).

13. An energy conserving method for monitoring heart muscle electrical activity of a patient as recited in claim 10 wherein steps b), c), d), e) and g) are performed at a relatively lower level of energy consumption and step f) is performed at a relatively higher level of energy consumption.

14. An energy conserving method for monitoring heart muscle electrical activity of a patient as recited in claim 13 wherein said relatively lower level of energy consumption has a substantially longer duration than said relatively higher level of energy consumption.

15. An energy conserving method for monitoring heart muscle electrical activity of a patient as recited in claim 10 wherein said third data set is evaluated to determine validity of said first analog signal and said second data set is evaluated to determine said ST segment deviation.

16. An energy conserving method for monitoring heart muscle electrical activity of a patient as recited in claim 10 further comprising repeating steps a) - g) for each succeeding analog electrical heart muscle signal.

17. An energy conserving method for monitoring heart muscle electrical activity of a patient as recited in claim 16 further comprising discharging said first data set from said temporary memory if said ST segment deviation does not exceed a predetermined threshold ST segment deviation.

18. An energy conserving method for monitoring heart muscle electrical activity of a patient as recited in claim 16 further comprising storing said first data set and said ST segment deviation in a permanent memory if said ST segment deviation exceeds a predetermined threshold ST segment deviation.

19. An energy conserving method for monitoring heart muscle electrical activity of a patient as recited in claim 18 further comprising transferring said first data set and said ST segment deviation stored in said permanent memory to a memory of a data transmission unit disassociated from said signal processing unit.

* * * * *